(12) United States Patent
Gusek et al.

(10) Patent No.: US 11,589,600 B2
(45) Date of Patent: Feb. 28, 2023

(54) PROCESS FOR OBTAINING CITRUS FIBER FROM CITRUS PEEL

(71) Applicant: Cargill, Incorporated, Wayzata, MN (US)

(72) Inventors: Todd Walter Gusek, Crystal, MN (US); Jacques André Christian Mazoyer, Carentan (FR); David Hiram Reeder, Chanhassen, MN (US); Joël René Pierre Wallecan, Vilvoorde (BE)

(73) Assignee: Cargill, Incorporated, Wayzata, MN (US)

( * ) Notice: Subject to any disclaimer, the term of this patent is extended or adjusted under 35 U.S.C. 154(b) by 56 days.

(21) Appl. No.: 15/882,533

(22) Filed: Jan. 29, 2018

(65) Prior Publication Data
US 2018/0153199 A1    Jun. 7, 2018

Related U.S. Application Data

(62) Division of application No. 14/372,354, filed on Jul. 15, 2014, now abandoned.

(51) Int. Cl.
*A23L 19/00* (2016.01)
*A23L 33/22* (2016.01)
(Continued)

(52) U.S. Cl.
CPC ............ *A23L 19/07* (2016.08); *A23D 7/0053* (2013.01); *A23D 7/0056* (2013.01); *A23D 9/007* (2013.01); *A23K 10/30* (2016.05); *A23K 10/37* (2016.05); *A23K 20/10* (2016.05); *A23K 20/163* (2016.05); *A23L 2/52* (2013.01); *A23L 29/206* (2016.08);
(Continued)

(58) Field of Classification Search
CPC ...... A23K 10/30; A23K 20/163; A23K 20/10; A23K 10/37; A61Q 19/00; A23L 19/07; A23L 33/22; A23L 33/21; A23L 29/206; A23L 2/52; C11D 7/44; C11D 3/382; A61K 47/46; A61K 8/97; A61K 2800/48; A61K 2800/85; A23D 9/007; A23D 7/0056; A23D 7/0053; A23V 2002/00; Y02P 60/877
See application file for complete search history.

(56) References Cited

U.S. PATENT DOCUMENTS 3,658,790 A    4/1972  Bernardin
5,213,836 A    5/1993  McGillivray
(Continued)

FOREIGN PATENT DOCUMENTS

CN    101297687 A    11/2008
CN    101797037 A    8/2010
(Continued)

OTHER PUBLICATIONS

"Mathmatical Modeling of Food Processing", ed. Mohammed M Farid, Taylor & Francis Group 2010, p. 53 and related citations.
(Continued)

*Primary Examiner* — Subbalakshmi Prakash

(57) ABSTRACT

A process is disclosed for obtaining citrus fiber from citrus peel. Citrus fiber is obtained having a c* close packing concentration value of less than 3.8 wt % anhydrous base. The citrus fiber can be used in food products, feed products, beverages, personal care products, pharmaceutical products or detergent products.

14 Claims, 1 Drawing Sheet

(51) Int. Cl.

| | |
|---|---|
| *A23L 33/21* | (2016.01) |
| *A23L 29/206* | (2016.01) |
| *A23K 20/10* | (2016.01) |
| *A23K 10/37* | (2016.01) |
| *A23K 10/30* | (2016.01) |
| *A61Q 19/00* | (2006.01) |
| *A23K 20/163* | (2016.01) |
| *A61K 47/46* | (2006.01) |
| *C11D 3/382* | (2006.01) |
| *A23L 2/52* | (2006.01) |
| *A23D 9/007* | (2006.01) |
| *A23D 7/005* | (2006.01) |
| *A61K 8/97* | (2017.01) |
| *C11D 7/44* | (2006.01) |
| *A23L 29/231* | (2016.01) |
| *A61K 8/9789* | (2017.01) |

(52) U.S. Cl.
CPC ............. *A23L 29/231* (2016.08); *A23L 33/21* (2016.08); *A23L 33/22* (2016.08); *A61K 8/97* (2013.01); *A61K 8/9789* (2017.08); *A61K 47/46* (2013.01); *A61Q 19/00* (2013.01); *C11D 3/382* (2013.01); *C11D 7/44* (2013.01); *A23V 2002/00* (2013.01); *A61K 2800/10* (2013.01); *A61K 2800/48* (2013.01); *A61K 2800/805* (2013.01); *A61K 2800/85* (2013.01); *Y02P 60/87* (2015.11)

(56) References Cited

U.S. PATENT DOCUMENTS

| | | | | |
|---|---|---|---|---|
| 5,964,983 | A | 10/1999 | Dinand | |
| 6,183,806 | B1 | 2/2001 | Ficca | |
| 7,094,317 | B2 | 8/2006 | Lundberg | |
| 2004/0086626 | A1 | 5/2004 | Lundberg | |
| 2005/0074542 | A1* | 4/2005 | Lundberg | D21C 3/02 426/658 |
| 2006/0115564 | A1* | 6/2006 | Passarelli | A21D 2/36 426/481 |
| 2009/0260768 | A1 | 10/2009 | Kim | |
| 2014/0356463 | A1 | 12/2014 | Gusek | |
| 2018/0009749 | A1 | 1/2018 | Qin et al. | |

FOREIGN PATENT DOCUMENTS

| | | | | |
|---|---|---|---|---|
| CN | 101014252 | B | | 3/2011 |
| CN | 101863955 | B | | 3/2015 |
| EP | 0295865 | B1 | | 1/1994 |
| EP | 0485030 | B1 | | 9/1995 |
| EP | 2002732 | A1 | | 12/2008 |
| EP | 2597968 | B1 | | 8/2018 |
| EP | 3372093 | B1 | | 7/2019 |
| WO | WO-9427451 | A1 * | 12/1994 | A23L 2/62 |
| WO | WO-9733688 | A1 * | 9/1997 | A61L 15/40 |
| WO | 0117376 | | | 3/2001 |
| WO | 2006033697 | | | 3/2006 |
| WO | 2008062057 | | | 5/2008 |
| WO | 2009075851 | | | 6/2009 |
| WO | 2010060778 | | | 6/2010 |
| WO | 2011131457 | A1 | | 10/2011 |
| WO | 2012016190 | A1 | | 2/2012 |
| WO | 2012016201 | A2 | | 2/2012 |
| WO | 2013109721 | A2 | | 7/2013 |
| WO | 2017019752 | | | 2/2017 |

OTHER PUBLICATIONS

"Microwave Release of Pectin for Orange Peel Albedo Using a Close Vessel Reactor System", Luzio, G. Proc. Fla. State Hort, Soc, 121:315-319, 2008.
"Multiple Emulsions" ed. Abraham Aserin: Chapter 2.4 in parts.
"Processed and Derived Products of Oranges" by CM Lanza. Encyclopedia of Food and Sciences Nutrition (2003) pp. 1346-1354.
Abstract band Dietan' Fibre—2000, Dublin, Ireland, accompanying document for proving the publication date of Fischer 2000 Poster.
Anton Paar instruction Manual MCR series, Feb. 2016.
Curriculum Vitae of Prof. Dr. Stephan Drusch.
Declaration of Dr. Joel Wallecan.
Delivery Documents for "Herbacel AQ plus Citrus" from Nov. 2009.
Dr. Wallecan's CV.
Excerpt from the textbook "Rheologie Handbuch", Thomas G. Mezger, Vincents Network, Hannover, Germany, 2008, pp. 208-210.
Expert Opinion of Prof. Dr. Stephan Drusch.
Fischer 2000 Poster "Functional Properties of Herbacel AQ Plus Fruit Fibers" for Dietary Fibre 2000, Dublin, Ireland.
Lab Report 156/17.
Laboratory report 086/20 first supplement, generated by the R&D department of Herbstreith & Fox, Apr. 1, 2020.
Laboratory report 086/20, generated by the R&D department of Herbstreith & Fox, Mar. 3, 2020.
Laboratory report regarding the influence of different measuring geometries on the viscosity measurement.
Product Specification of the Herbacel AQ Plus Citrusfaser, lot No. 3202046, Mar. 21, 2002.
Reply to Written Opinion prepared by the EPO for EP 3372093 A1, submitted by Cargill on Feb. 27, 2019.
Submission in Proceedings EP 11741728.7 (Oct. 22, 2013).
Submission in proceedings EP 2597968 B1 (Oct. 22, 2013).
U.S. Appl. No. 61/369,207, unpublished, Gusek et al.
Priority application in EP2597968B1, Gusek et al., unpublished.
Article: Einsatz der Druckhomogenisierung zur Herstellung von zellstrukturiertem Apfelmaterial, Herbert Kunzek et al., Zellschrift fur Lebensmittel Undersuchung und—Forschung Springer Verlag 1994.
Citrofiber DF-50 Classification; download from http:/www.faqs.org/rulings/rulings1991NY0860474.html on Apr. 19, 2019 (Mar. 22, 1991).
Dietary Fiber, Dublin 2000—Conference Announcement.
Experimental Data.
Ferguson, R.R. et al., Dietary Citrus Fibers, ASME 1987 Citrus Engineering Conference Lakeland Florida, USA (Mar. 23, 1976).
Herbafood "Fruit and More", Flussiges Obst, pp. 1-6 (May 2002).
Mueller, S. S. et al. "Material properties of processed fruit and vegetables", Zeitschrift fur Lebensmitteluntersuchungund-Forschung, vol. 206, pp. 264-272 (1998).
Original Article Fischer, J. Flussiges Obst 2002, 5: 319-321.
Scientific Report. (Apr. 15, 2019).
Steenecken, P.A.M., Carbohydrate Polymers, 11, 23, 1989.
Supercritical CO2—A Green Solvent.
Table of Contents of Journal "Flussiges Obst", May 2002.
Test Report NR. 156/17 Vom Oct. 11, 2018.
The Influence of Mechanical and Enzymatic Disintegration of Carrots on the Structure and Properties of Cell Wall Materials, Claudia Pickardt, Gerhard Dongowski and Herbert Kunzek, Eur Food Res Technol (2004).
Title Page of Journal Flussiges Obst, May 2002.
Vandeputte et al., J. Ceral. Sci., 38, 53, 2003.

* cited by examiner

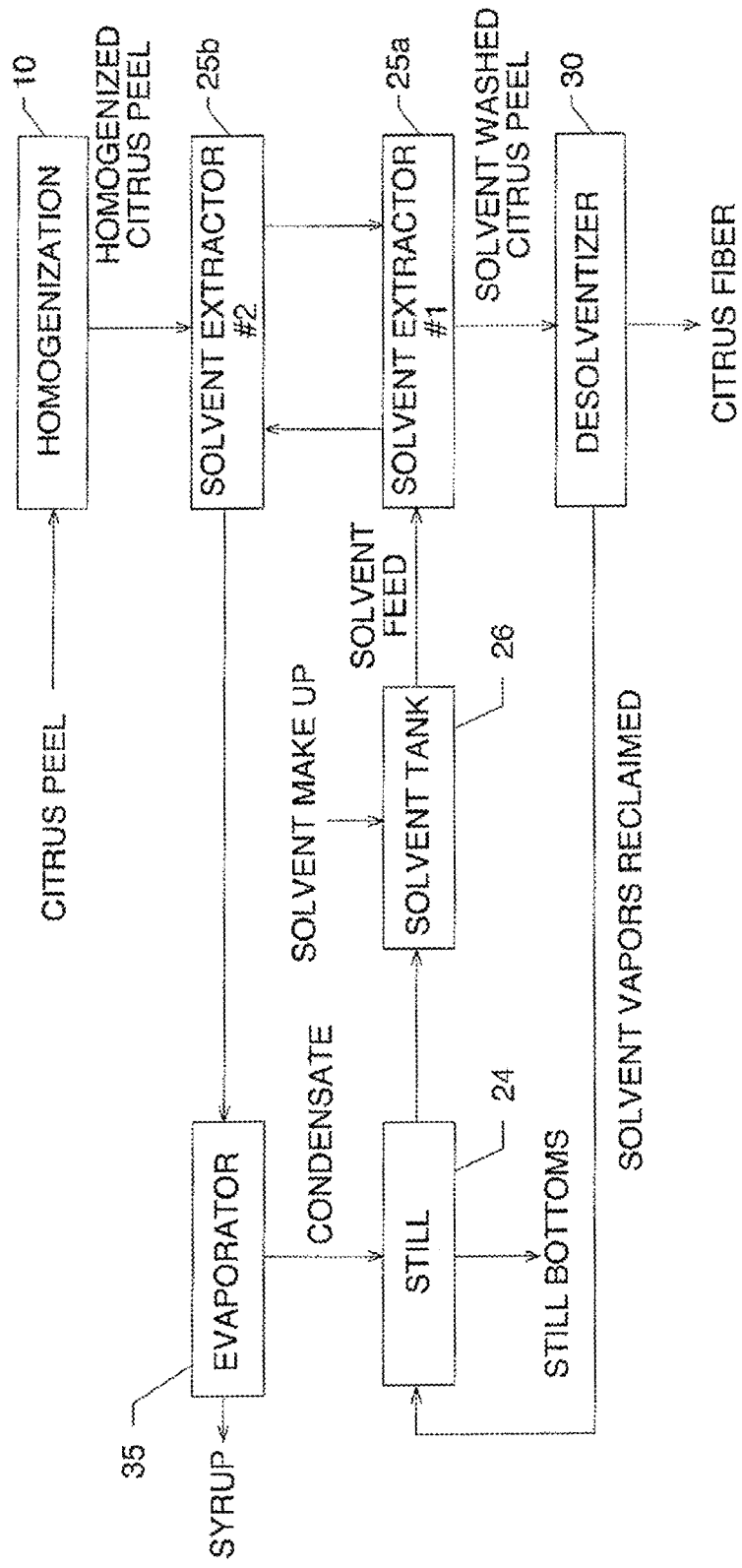

PROCESS FOR OBTAINING CITRUS FIBER FROM CITRUS PEEL

CROSS-REFERENCE TO RELATED APPLICATIONS

This application is a Divisional of U.S. patent application Ser. No. 14/372,354, filed Jul. 15, 2014, and entitled PROCESS FOR OBTAINING CITRUS FIBER FROM CITRUS PEEL, which claims the benefit of PCT Patent Application, Serial No. PCT/US13/021888, filed Jan. 17, 2013, entitled PROCESS FOR OBTAINING CITRUS FIBER FROM CITRUS PEEL, which claims the benefit of Provisional Patent Application Ser. No. 61/588,915, filed Jan. 20, 2012, entitled PROCESS FOR OBTAINING CITRUS FIBER FROM CITRUS PEEL, which applications are hereby incorporated by reference herein in their entirety.

TECHNICAL FIELD

The present invention is directed to a process for obtaining citrus fiber from citrus peel. The resulting dried citrus fiber is useful as a food additive in food products, feed products and beverages. The citrus fiber is also useful in personal care, pharmaceutical or detergent products.

BACKGROUND OF THE INVENTION

Citrus peel is a waste product from the juice industry or is a by-product from the pectin process. Pectin can be obtained from various raw materials like citrus peels using a specific treatment in hot acid aqueous conditions. Citrus include e.g. lemon, orange, lime, grape fruit of which lemon is the most commonly used. The peels obtained from the juice industry are typically subjected to another treatment to extract juice and oil, and are then dried. These peels are typically used for cattle feed. The peels obtained from the pectin process, after extraction of pectin, are of even lower economical value.

It would thus be desirable to improve the economical value of this product. One approach is to improve the functional properties of the fibers which can be derived from citrus peel. However, the properties of existing citrus peel fibers can still be improved.

Hence, it is an object of the present invention to develop a process for obtaining citrus fiber from citrus peel having improved properties versus the citrus fiber of the prior art. It is further an object of the present invention to obtain a citrus fiber which has good hydration ability and viscosifying properties.

SUMMARY OF THE INVENTION

The present invention, according to one aspect, is directed to a process for obtaining citrus fiber from citrus peel. In one embodiment, citrus peel is treated to obtain homogenized citrus peel. The process further comprises a step of washing the homogenized citrus peel with an organic solvent to obtain organic solvent washed citrus peel. The organic solvent washed citrus peel is desolventized and dried, and citrus fiber is recovered.

In another aspect, the present invention is directed to a citrus fiber having a c* close packing concentration value of less than 3.8 wt % anhydrous base. In a preferred embodiment, the citrus fiber has a moisture content of from about 5% to about 15%. In another preferred embodiment, the citrus fiber has a viscosity of at least 1000 mPa·s, wherein said citrus fiber is dispersed in standardized water at a mixing speed of from about 800 rpm to about 1000 rpm, preferably about 900 rpm, to a 3 w/w % citrus fiber/standardized water solution, and wherein said viscosity is measured at a shear rate of 5 $s^{-1}$ at 20° C. In yet another preferred embodiment, the citrus fiber has a CIELAB L* value of at least about 90.

In yet another aspect, the present invention is directed to a blend of citrus fiber of the present invention and plant-derived (e.g. derived from cereals) fiber, citrus fiber obtained from citrus pulp and combinations thereof.

In yet another aspect, the present invention is directed to a food product, a feed product, a beverage, a personal care product, pharmaceutical product or a detergent product comprising the citrus fiber according to the present invention.

In yet another aspect, the present invention is directed to the use of the citrus fiber as a texturiser or viscosifier in food products, feed products, beverages, personal care product, pharmaceutical product or detergent product.

BRIEF DESCRIPTION OF THE DRAWINGS

FIG. 1 is a schematic illustration of a process in accordance with a preferred embodiment of the present invention.

DETAILED DESCRIPTION OF THE INVENTION

In one aspect, the present invention is directed to a process for obtaining citrus fiber from citrus peel.

The term "citrus peel," as used herein, refers to the pectinaceous and cellulosic material contained in the outer portion of citrus fruit. It can be a waste product from the juice industry. It can also be a co-product of the pectin industry, and is sometimes then referred to as "spent peel". The term "citrus fiber," as used herein, refers to a fibrous component obtained from citrus peel.

The process according to the present invention may be used for obtaining citrus fiber from citrus peel from a wide variety of citrus fruit, non-limiting examples of which include oranges, tangerines, limes, lemons, and grapefruit. In one preferred embodiment, citrus fiber is obtained from lemon peel.

In the process according to the present invention, citrus peel is treated to obtain homogenized citrus peel. In a preferred embodiment, spent peel is used as starting material. Optionally, the citrus pool may be washed with water prior to homogenization. Sometimes, citrus peel may be provided in a frozen or dried state which requires thawing or rehydration prior to homogenization. Preferably, the citrus peel is adjusted with water to a dry matter content of 5 wt % or less. While not intending to be bound to any theory, it is believed that the homogenization treatment causes disruption and disintegration of whole peel cells and cell fragments. Homogenization can be effected by a number of possible methods including, but not limited thereto, high shear treatment, pressure homogenization, colloidal milling, intensive blending, extrusion, ultrasonic treatment, and combinations thereof. Preferably, the power input (power per unit volume) for effecting homogenization is at least about 1000 kW per $cm^3$ of citrus peel.

In a preferred embodiment of the present invention, the homogenization treatment is a pressure homogenization treatment. Pressure homogenizers typically comprise a reciprocating plunger or piston-type pump together with a homogenizing valve assembly affixed to the discharge end of the homogenizer. Suitable high pressure homogenizers include high pressure homogenizers manufactured by GEA Niro Soavi, of Parma (Italy), such as the NS Series, or the homogenizers of the Gaulin and Rannie series manufactured by APV Corporation of Everett, Mass. (US).

During the pressure homogenization, the citrus peel is subjected to high shear rates as the result of cavitations and turbulence effects. These effects are created by the citrus peel entering the homogenizing valve assembly from the pump section of the homogenizer at a high pressure (and low velocity). Suitable pressures for the process of the present invention are from about 50 bar to about 1000 bar.

Depending on the particular pressure selected for the pressure homogenization, and the flow rate of the citrus peel through the homogenizer, the citrus peel may be homogenized by one pass through the homogenizer. However, more than one pass of the citrus peel may be required.

In one embodiment, the citrus peel is homogenized by a single pass through the homogenizer. In a single pass homogenization, the pressure used is preferably from about 300 bar to about 1000 bar, more preferably from about 400 bar to about 800 bar, even more preferably from about 500 bar to about 750 bar.

In another preferred embodiment, the citrus peel is homogenized by multiple passes through the homogenizer, preferably at least 2 passes, more preferably at least 3 passes through the homogenizer. In a multipass homogenization, the pressure used is typically lower compared to a single-pass homogenization and preferably from about 100 bar to about 600 bar, more preferably from about 200 bar to about 500 bar, even more preferably from about 300 bar to about 400 bar.

Optionally, the citrus peel may be subjected to a heat treatment prior to homogenization. Preferably, the temperature used in the heat treatment can vary from about 50° C. to about 140° C. for a period of from about 1 second to about 3 minutes. The heat treatment may be used for pasteurization of the citrus peel. For pasteurization, the heat treatment preferably employs a temperature of from about 65° C. to about 140° C., preferably from about 80° C. to about 100° C. for a period of from about 2 seconds to about 60 seconds, preferably from about 20 seconds to about 45 seconds. Pasteurization is preferred to inactivate pectinesterases for preventing cloud loss and to inactivate spoilage microorganisms for enhancing storage stability.

The homogenized citrus peel is then contacted with an organic solvent. In one aspect, the organic solvent extracts water, flavors, odors, colors and the like from the citrus peel. The solvent should preferably be polar and water-miscible to better facilitate removal of the desired components. Available solvents may include lower alcohols such as methanol, ethanol, propanol, isopropanol, or butanol. Preferred solvents are ethanol, isopropanol, and combinations thereof. The solvent may be provided in aqueous solution. The concentration of solvent in the solvent solution most often ranges from about 70 wt % to about 100 wt %. In one embodiment, a 75 wt % aqueous ethanol solution is used as solvent. In a preferred embodiment, a 90 wt % aqueous ethanol solution is used as solvent. In yet another preferred embodiment, isopropanol is used as a solvent, preferably an aqueous isopropanol solution. In general, solvents will remove water-soluble components at lower concentrations and oil-soluble components at higher concentrations. Optionally, a more non-polar co-solvent may be added to the aqueous alcohol to improve the recovery of oil-soluble components in the citrus peel. Examples of such non-polar solvents include ethyl acetate, methyl ethyl ketone, acetone, hexane, methyl isobutyl ketone and toluene. The more non-polar solvents may be added at up to about 20% of the solvent mixture. Many solvents, such as ethanol, have a lower heat of vaporization than that of water, and therefore require less energy to volatilize than would be needed to volatilize an equivalent mass of water. The solvent preferably is removed and reclaimed for reuse.

Preferably, the citrus peel is contacted with organic solvent at a solids-to-solvent weight ratio of at least about 0.25:1, preferably at least about 0.5:1, and often at least about 0.75:1, from about 1:1 to about 5:1, or from about 1.5:1 to about 3:1, based on the wet weight of the solids. In one embodiment, the solids-to-solvent ratio is about 2:1.

Extraction can be accomplished using a single stage but preferably is performed using multi-stage extraction, e.g., a two-, three-, or four-staged extraction process, and preferably using countercurrent extraction. There is no particular upper limit contemplated on the number of extraction stages that may be used. FIG. 1 schematically illustrates a preferred embodiment in which a two-stage countercurrent extraction process employs first and second solvent extractors 25a and 25b, respectively.

After homogenization 10, homogenized citrus peel is fed into the second extractor 25b. An aqueous ethanol or isopropanol solvent is fed from a solvent tank 26 into the first solvent extractor 25. Spent solvent from the first solvent extractor 25a is fed into the second solvent extractor 25b, while the extracted citrus peel from the second solvent extractor 25b are fed into the first solvent extractor 25a. Spent solvent from the second solvent extractor 25b may be fed into an evaporator 35 (optional) to separate solids (e.g., sugars, acids, colors, flavors, citrus oils, etc.) from the spent solvent, which can be condensed and returned to a still 24. Still bottoms (predominately water) are separated and removed.

After each extraction stage, liquid is preferably further removed. One suitable device is a decanter centrifuge. Alternatively, a sieve, a belt filter press or other device suitable for removing liquids, may be used.

Citrus peel from the first solvent extractor 25a is fed to a desolventizer 30. The desolventizer 30 removes solvent and water from the solids remaining after extraction, enabling the solvent to be reclaimed for future use and also ensuring that the product is safe for milling and commercial use. The desolventizer 30 can employ indirect heat to remove significant amounts of solvent from the solid residue. Alternatively, direct heat can be provided for drying, e.g., by providing hot air from flash dryers or fluidized bed dryers. Direct steam may be employed, if desired, to remove any trace amounts of solvent remaining in the solids. Vapors from the desolventizer 30 preferably are recovered and fed to the still 24 to reclaim at least a portion of the solvent.

Retention time in each extraction step may vary over a wide range but can be about 5 minutes or less per extraction step. The temperature in the solvent extractor(s) depends on such factors as the type of solvent used but most often ranges from about 4° C. to about 85° C. at atmospheric pressure. Temperatures can be appropriately increased or decreased for operation under super- or sub-atmospheric pressures. Optionally, techniques such as ultra-sound are used for enhancing efficiency of the extraction process. By maintaining a closed system, solvent losses during extraction, desolventizing, and distillation can be minimized. Preferably, at least about 70 wt % of the solvent is recovered and reused. A solvent make-up stream delivers fresh solvent into the solvent tank 26 to replenish any solvent that is not recovered.

In a preferred embodiment, the process according to the present invention further comprises a comminuting or pulverizing step prior to desolventizing and drying. Suitable methods include, but are not limited to, grinding, milling, crushing, high speed mixing, or impingement. Comminution or pulverization can be beneficial to disintegrate any clumps or aggregates that are left after the removal of liquid with the belt filter pressing step. This step furthermore facilitates the removal of solvent. While not wishing to be bound by theory, it is believed that comminution or pulverization further opens the fibers. As a result of this, the solvent is more uniformly distributed and easier to be removed in the subsequent desolventization and drying step. In yet another preferred embodiment, the comminuting or pulverizing step is used in combination with adding and dispersing water or a blend of water and an organic solvent (as described hereinbefore) to enhance desolventization and drying, and achieve the desired humidity in the finally obtained citrus fiber for a particular end use.

In another preferred embodiment, the process according to the present invention further comprises a comminuting or pulverizing step after drying. This post-drying comminuting or pulverizing step may be carried out to further reduce the particle size of the citrus fiber, to improve flowability, dispersability, and/or hydration properties.

In yet another preferred embodiment, the process according to the present invention further comprises the step of subjecting the citrus peel to a processing aid. Preferably, the processing aid is selected from the group consisting of enzymes, acids, bases, salts hydrocolloids, vegetable fiber, bleaching agent, and combinations thereof. In one embodiment, the processing aid is mixed with the citrus peel prior to homogenization. In another embodiment, the processing aid is added after homogenization.

In one aspect of the present invention, the processing aid may be used to tailor the properties of the finally obtained citrus fiber.

Preferred enzymes include, but are not limited thereto, pectinase, protease, cellulase, hemicellulase and mixtures thereof. When enzymes are used, they are to be used prior to any heat treatment that would inactivate them, and preferably also prior to homogenization. Inactivation by heat treatment is however desired once the desired effect is achieved.

Preferred acids include, but are not limited thereto, citric acid, nitric acid, oxalic acid, ethylenediaminetetraacetic acid and combinations thereof. Citric acid is however most preferred as it is a food grade acid.

A preferred base is caustic soda. Caustic soda improves the swelling behavior and the texurising properties of the citrus fiber. Caustic soda is preferably added after homogenization.

A preferred salt is sodium chloride.

Preferred hydrocolloids include, but are not limited thereto, pectin, alginate, locust bean gum, xanthan gum, guar gum, carboxymethylcellulose and combinations thereof.

A bleaching agent may further enhance the color properties (i.e. render the citrus fiber whiter). A preferred bleaching agent is hydrogen peroxide.

The citrus fiber obtained by the process according to the present invention has improved properties over other citrus fibers from the prior art. Especially, the citrus fiber has good swelling behavior, hydration ability and viscosifying properties. It is capable of building viscosity under relatively low shear in aqueous media.

The citrus fiber of the present invention has a c* close packing concentration of less than 3.8 wt %, anhydrous basis. Preferably, the c* close packing concentration is less than 3.6, even more preferably less than 3.4 wt %, and most preferably less than 3.2 wt %, anhydrous basis. The determination of the c* close packing concentration is described in the test method section herein below.

The citrus fiber preferably has a moisture content of about 5% to about 15%, more preferably from about 6% to about 14%. Preferably, at least about 90% of the volume of the particles have a diameter of less than about 1000 micrometers, preferably from about 50 micrometers to about 1000 micrometers, more preferably from about 50 micrometers to about 500 micrometers, even more preferably from about 50 micrometers to about 250 micrometers.

The citrus fiber preferably has a viscosity of at least about 1000 mPa·s, wherein said citrus fiber is dispersed in standardized water at a mixing speed of from 800 rpm to 1000 rpm, preferably 900 rpm, to a 3 w/w % citrus fiber/standardized water solution, and wherein said viscosity is measured at a shear rate of 5 $s^{-1}$ at 20° C. Preferably, the viscosity at a shear rate of 5 $s^{-1}$ at 20° C. is at least about 2000 mPa·s, more preferably at least about 3000 mPa·s, even more preferably at least 4000 mPa·s, even more preferably at least 5000 mPa·s and up to 15000 mPa·s. The preparation of the standardized water, and the method for measuring viscosity is described in the test method section herein below.

The citrus fiber according to the present invention further has good emulsification properties.

In a preferred embodiment, the citrus fiber of the present invention also has excellent whiteness properties. The citrus fiber may have a CIELAB L* value of at least about 85, preferably of at least about 90, more preferably at least about 92, even more preferably at least about 93. Preferably, the citrus fiber has a CIELAB b* value of less than about 20, even more preferably of less than about 15. The method for determining the CIELAB L* and b* values is described in the test method section herein below.

The citrus fiber according to the present invention can be blended with other fibers, such as plant-derived (e.g. from vegetables, grains/cereals) fibers, with other citrus fibers such as citrus fiber obtained from citrus pulp, or combinations thereof. The blend can be in dry or liquid form.

In another aspect, the citrus fiber of the present invention and the blends described hereinbefore may be used in food applications, feed applications, beverages, personal care products, pharmaceutical products or detergent products. The amount of citrus fiber (or blend) to be used depends on the given application and the desired benefit to be obtained, and lies within the knowledge of a skilled person.

Food applications may include, but are not limited to, dairy products, frozen products, bakery products, fats and oils, fruit products, confectionery, meat products, soups, sauces and dressings. Dairy products include, but are not limited to yoghurt, fromage frais, quark, processed cheese, dairy desserts, mousses. Frozen products include, but are not limited to, ice cream, sorbet, water ice. Bakery products include, but are not limited to, cakes, sweet goods, pastry, patisserie, extruded snacks, fried snacks. Fats and oils include, but are not limited to, margarines, low fat spreads, cooking fats. Fruit products include, but are not limited to, fruit preparations, yoghurt fruit preparations, conserves, jams, jellies. Sauces and dressings include, but are not limited to, egg yolk or egg-yolk derivatives containing oil/water emulsions such as mayonnaise, and ketchup. Confectionery includes, but is not limited to, candy, chocolate spreads, nut-based spreads. Meat products include, but are not limited to, chilled or frozen processed meat and poultry, preserved meat products, fresh sausage, cured sausage and salami.

Beverages may include concentrates, gels, energy drinks, carbonated beverages, non-carbonated beverages, syrups. The beverage can be any medical syrup or any drinkable solution including iced tea, and fruit juices, vegetable based juices, lemonades, cordials, nut based drinks, cocoa based drinks, dairy products such as milk, whey, yogurts, buttermilk and drinks based on them. Beverage concentrate refers to a concentrate that is in liquid form.

Personal care products may include cosmetic formulations, hair care products such as shampoos, conditioners, creams, styling gels, personal washing compositions, suncreams and the like.

Detergent products may include hard surface cleaning products, fabric cleaning or conditioning products, and the like.

Test Methods

1. Preparation of Standardised Water

Dissolve 10.0 g NaCl (e.g. Merck 1.06404.1000, CAS [7647-14-5]) and 1.55 g $CaCl_2 \cdot 2H_2O$ (e.g. Merck 1.02382.1000, CAS [10035-04-8]) in low conductivity water (e.g. milli-Q Ultrapure Millipore 18.2 MΩcm), and make up to 1 liter to prepare standardized water stock. Take a 100 ml aliquot of the standardized water stock and make up to 1 liter with low conductivity water.

2. Measuring c* Close Packing Concentration 2.1 Principle

Citrus fiber samples (n≥210) are wetted with ethylene glycol, dispersed in standardised tap water, and subjected to the MCR301 controlled shear stress (CSS) oscillatory test. The citrus fiber dispersions are measured by 0.25 w/w % increments in the range of 1.75-5.00 w/w %. The linear viscoelastic range (LVR) complex moduli G* is plotted against concentration. The close-packing concentration c* is determined via the two tangents crossover method on a linear scale.

2.2 Apparatus

Anton Paar MCR301 rheometer with coaxial cylinder configuration (TEZ 150P-CF Peltier at 20° C.) with vane probe ST24-2D/2V/2V-3D, grooved measuring cup CC27/T200/SS/P and circulating cooling water bath set at 15° C. The equipment must be clean and dry, and the MCR301 units must be turned on 30 minutes before use. Checks should be made according to the instruction manual of the supplier (see Instruction manual). The Circulator bath and pump should be at all times in use to avoid burning of the peltier unit. According to the manufacturer, the water bath must be filled with demineralised water containing maximum 30% of antifreeze (e.g. ethylene glycol).

RWD 20 Digital IKA stirrer and lower the paddle (4 bladed propeller 07 410 00)

600 ml Duran glass beaker (e 10 cm)

Laboratory balance having a precision of 0.01 g

Hard plastic soup spoon 2.3 Procedure

System Start-Up

Start up the circulator bath (filled with demineralised water+30% ethylene glycol (e.g. Merck 1.00949.1000, CAS [107-21-1])) and afterwards the rheometer according to the procedure explained in the instruction manual. Select the workbook and perform the initialisation procedure according to the instruction manual.

System Calibration

The standard calibration check procedure for the MCR301 is fully described in the instruction manual and should be performed according to the instruction manual. The MCR301 Instruments must be ready (initiated and all parameters checked) before testing the citrus fiber dispersions. The ST24 measuring system CSR should be set to 1 and the CSS value (Pa/mNm) should be fixed with certified calibration Newtonian oil (e.g. Cannon N100, available from Cannon Instrument Company, State College, Pa. 16803, USA).

Sample Preparation

Place a 600 ml glass beaker on the laboratory balance, and zero the balance.

Weigh into the beaker the required grams (x) of citrus fiber, to the nearest 0.01 g, according to the moisture content (m) of the citrus fiber sample: x=3c/[(100−m)/100], for any given concentration c in w/w % (samples starting at 1.75 w/w %, to 5.00 w/w % with 0.25 w/w % increments). The moisture content m should be determined by infra-red moisture balance (Sartorius MA 30), as weight loss at 105° C. with automatic timing, typically 3-4 g citrus fiber covering the entire bottom of the aluminum pan. The moisture content (m) of citrus fiber is in weight percent (w %).

Weigh into a second 600 mL beaker the required grams (w) of standardised tap water, to the nearest 0.1 g, according to the moisture of the citrus fiber sample: w=270.0−x Place the beaker with CPF on the laboratory balance, zero the balance, add 30.0 g (to the nearest 0.1 g) of ethylene glycol, put the beaker out of the balance and mix the content with the plastic spoon thereby wetting the whole powder (this operation is performed within 60 seconds).

Pour at once the standardised tap water on to the wet citrus fiber and mix the content with the plastic spoon by repeated clockwise and anti-clockwise rotations (this operation is performed within 60 seconds).

Position the glass beaker with its content (citrus fiber, ethylene glycol, standardised tap water) underneath a RWD 20 Digital IKA stirrer and lower the paddle (4 bladed propeller 07 410 00) into the paste until 2 cm from the bottom of the glass beaker.

Adjust the paddle speed (rpm) to 900 rpm and stir 10 minutes at 900 rpm.

Cover the beaker with aluminum foil and allow 24 hours rest prior measurement

Pour the required amount of CPF dispersion into the cylindrical cup of the rheometer and insert immediately the vane probe ST24 (starch cell probe) into the cylinder containing the CPF dispersion Sample Analysis Perform CSS oscillatory test with the MCR301 according to the manual instructions, with 2 segments:

segment 1: non recording, 10 minutes at 20° C. (equilibration)

segment 2: recording, 1971 seconds at 20° C., 50 measuring points integration time 100 to 10 seconds log, torque 1 to 10,000 µNm log, frequency 1 Hz Results At low stress, where the G* (versus stress) is showing constant plateau values, average the G* results over the linear viscoelastic range. Using the software "LVE Range", the end of the linear viscoelastic region in the CSS experiments can be determined.

Plot the LVR G* versus concentration. The first tangent at low concentration (below c*) has a much lower slope than the second tangent at high concentration (above c*). Using linear fitting (e.g. with Microsoft® Excel®), the crossover point of both tangents occurs at the c* close packing concentration.

3. Measuring Viscosity

Add citrus fiber to standardized water in a beaker with a paddle mixer to obtain a 3 wt % citrus fiber dispersion with a total volume of 300 mL Prior to adding the citrus fiber, create a vortex by adjusting the paddle speed to 900 rpm using an IKA Overhead Mechanical Stirrer RW20 equipped with a 4-bladed propeller stirrer. Then add the citrus fiber quickly (before the viscosity builds up) on the walls of the vortex under stirring (900 rpm using an IKA Overhead Mechanical Stirrer RW20 equipped with a 4-bladed propeller stirrer). Continue stirring for 15 minutes at 900 rpm. Store the sample for 12 hours at 20° C.

Then perform the viscosity test with a rheometer (e.g. Anton Paar MCR300), in accordance with the rheometer's instructions, in function of shear rate (from 0.01 to 100 $s^{-1}$) at 20° C.

The viscosity (mPa·s) is determined at a shear rate of 5 $s^{-1}$.

4. Measuring Colour (CIELAB L*, b* Values)

CIE L*a*b* (CIELAB) is the most complete color space specified by the International Commission on Illumination (Commission Internationale d'Eclairage). It describes all the colors visible to the human eye and was created to serve as a device independent model to be used as a reference. The L* and b* values of the citrus fiber are obtained by placing citrus fiber (in powder form) in the glass cell (fill the cell to about a half) of the colormeter and analyse the sample in accordance with the user's instructions of the colorimeter. The colorimeter used is a Minolta CR400 Colorimeter.

Example

| sample | c* (wt %, anhydrous base) |
|---|---|
| Citrus fiber according to the invention | 3.5 |
| Herbacel AQ-Plus Citrus Fibre N | 3.94 |
| Citri-Fi 100 | 4.04 |

Citri-Fi 100: orange fiber derived from orange pulp (Fiberstar Inc.)

Herbacel AQ-Plus Citrus Fibre N: lemon fibers derived from lemon peel (Herbstreith & Fox Inc).

What is claimed is:

1. A process for preparing citrus fibers from citrus spent peel, the process comprising:
   mixing citrus spent peel with a hydrocolloid processing aid selected from the group consisting of alginate, locust bean gum, xanthan gum, guar gum, carboxymethylcellulose, and combinations thereof, to obtain homogenized citrus spent peel wherein power input for effecting homogenization treatment is at least 1000 kW per $cm^3$ of citrus fiber;
   washing the homogenized citrus spent peel with an organic solvent at a solids-to-solvent ratio of at least about 0.25:1 to obtain organic solvent washed citrus spent peel;
   comminuting or pulverizing the organic solvent washed citrus spent peel;
   desolventizing and drying the comminuted or pulverized citrus spent peel;
   comminuting or pulverizing the desolventized and dried citrus spent peel; and
   recovering citrus fiber from the comminuted or pulverized, desolventized, and dried citrus spent peel, wherein the citrus fiber has a c* close packing concentration value of less than 3.8 wt %.

2. The process according to claim 1, wherein the homogenization treatment comprises pressure homogenization using a pressure of from 50 bar to 1000 bar.

3. The process according to claim 2, wherein the homogenization treatment is a single-pass pressure homogenization using a pressure of from 300 bar to 1000 bar.

4. The process according to claim 2, wherein the homogenization treatment is a multi-pass pressure homogenization comprising at least 2 passes, using a pressure of from 100 bar to 600 bar.

5. The process according to claim 1, wherein the citrus spent peel is subjected to a heat treatment prior to the homogenization treatment at a temperature of from 5° C. to 140° C. for a period of 1 second to 3 minutes.

6. The process according to claim 1, further comprising treating the citrus spent peel with a bleaching agent.

7. The process according to claim 6, wherein the bleaching agent comprises hydrogen peroxide.

8. The process according to claim 2, wherein the homogenization treatment is a multi-pass pressure homogenization comprising at least 2 passes, using a pressure of from 30 bar to 400 bar.

9. The process according to claim 8, wherein the homogenization treatment is a multi-pass pressure homogenization comprising at least 3 passes, using a pressure of from 300 bar to 400 bar.

10. The process according to claim 1, wherein the organic solvent is selected from the group consisting of methanol, ethanol, propanol, isopropanol, butanol, and combinations thereof.

11. The process according to claim 1, wherein the organic solvent is selected from the group consisting of ethanol, isopropanol, and combinations thereof.

12. The process according to claim 10, wherein the organic solvent further comprises a non-polar organic co-solvent.

13. The process according to claim 12, wherein the non-polar organic co-solvent comprises up to 20 wt % of the mixture of organic solvent and non-polar co-solvent.

14. The process according to claim 12, wherein the non-polar organic co-solvent comprises ethyl acetate, methyl ethyl ketone, acetone, hexane, methyl isobutyl ketone, toluene, or a mixture thereof.

* * * * *